(12) United States Patent
Abe et al.

(10) Patent No.: US 6,287,757 B1
(45) Date of Patent: Sep. 11, 2001

(54) AMINO ACID-TREHALOSE COMPOSITION

(75) Inventors: Takashi Abe, 16-15, Minami-machi 1-chome, Warabi-shi, Saitama-ken (JP); Koji Iida, Tokyo; Hiroshi Tsuchita, Hoya, both of (JP)

(73) Assignees: Riken, Wako; Meiji Milk Products Co., Ltd., Tokyo; Takashi Abe, Warabi, all of (JP)

( * ) Notice: Subject to any disclaimer, the term of this patent is extended or adjusted under 35 U.S.C. 154(b) by 0 days.

(21) Appl. No.: 09/379,361

(22) Filed: Aug. 23, 1999

(30) Foreign Application Priority Data

Aug. 24, 1998 (JP) .................................... 10-237485

(51) Int. Cl.⁷ .............................. C12Q 1/00; A01N 43/04
(52) U.S. Cl. ................................. 435/4; 514/53; 514/561; 426/656; 426/658
(58) Field of Search .................................... 426/656, 658; 514/53, 561; 435/4

(56) References Cited

U.S. PATENT DOCUMENTS 4,554,251  11/1985  Hink, Jr. .............................. 435/240

FOREIGN PATENT DOCUMENTS

| 06227975 | * | 8/1994 | (JP) . |
| 06279227 | * | 10/1994 | (JP) . |
| WO 96/28540 | | 9/1996 | (WO) . |
| WO 97/25060 | | 7/1997 | (WO) . |

OTHER PUBLICATIONS

Patent Abstracts of Japan, vol. 018, No. 316 (C–1213), Jun. 16, 1994, JP 06 070718, Mar. 15, 1994.

Derwent Abstracts, AN 1995–057293, JP 06 336426, Dec. 6, 1994.

Derwent Abstracts, AN 1992–156230, JP 04 095026, Mar. 27, 1992.

Hiroshi Tsuchita, et al., "Effects of a Vespa Amino Acid Mixture Identical to Hornet Larval Saliva on the Blood Biochemical Indices of Running Rats", Nutrition Research, vol. 17, No. 6, (1997), pp. 999–1012.

Abe et al. "Comparative study of the composition of hornet larval saliva, its effect on behavior and role of trophallaxis", Comp. Biochem. Physiol., C. Comp. Pharmacol. Toxicol., vol. 99C(102): 79–84, Abstract only, 1991.*

Hu et al. "A study on the host–searching kairomone of Apanteles cypris Nixon", Kunchong Xuebao, vol. 30(1): 31–40, Abstract only, 1987.*

* cited by examiner

*Primary Examiner*—Louise N. Leary
(74) *Attorney, Agent, or Firm*—Oblon, Spivak, McClelland, Maier & Neustadt, P.C.

(57) ABSTRACT

An amino acid-trehalose composition comprising an amino acid composition which comprises proline, alanine, glycine, valine, threonine, leucine, histidine, lysine, isoleucine, arginine, phenylalanine, tyrosine, and tryptophan; and trehalose. The amino acid-trehalose composition has effects of compensating the reduction of the blood level of amino acids associated with severe exercise, of improving the exercise, of reducing the degree of fatigue after exercise and of recovering from fatigue. In addition, the administration of the composition permits the inhibition of the consumption of amino acids associated with exercise and any induction of fatigue accompanied by exercise.

28 Claims, 3 Drawing Sheets

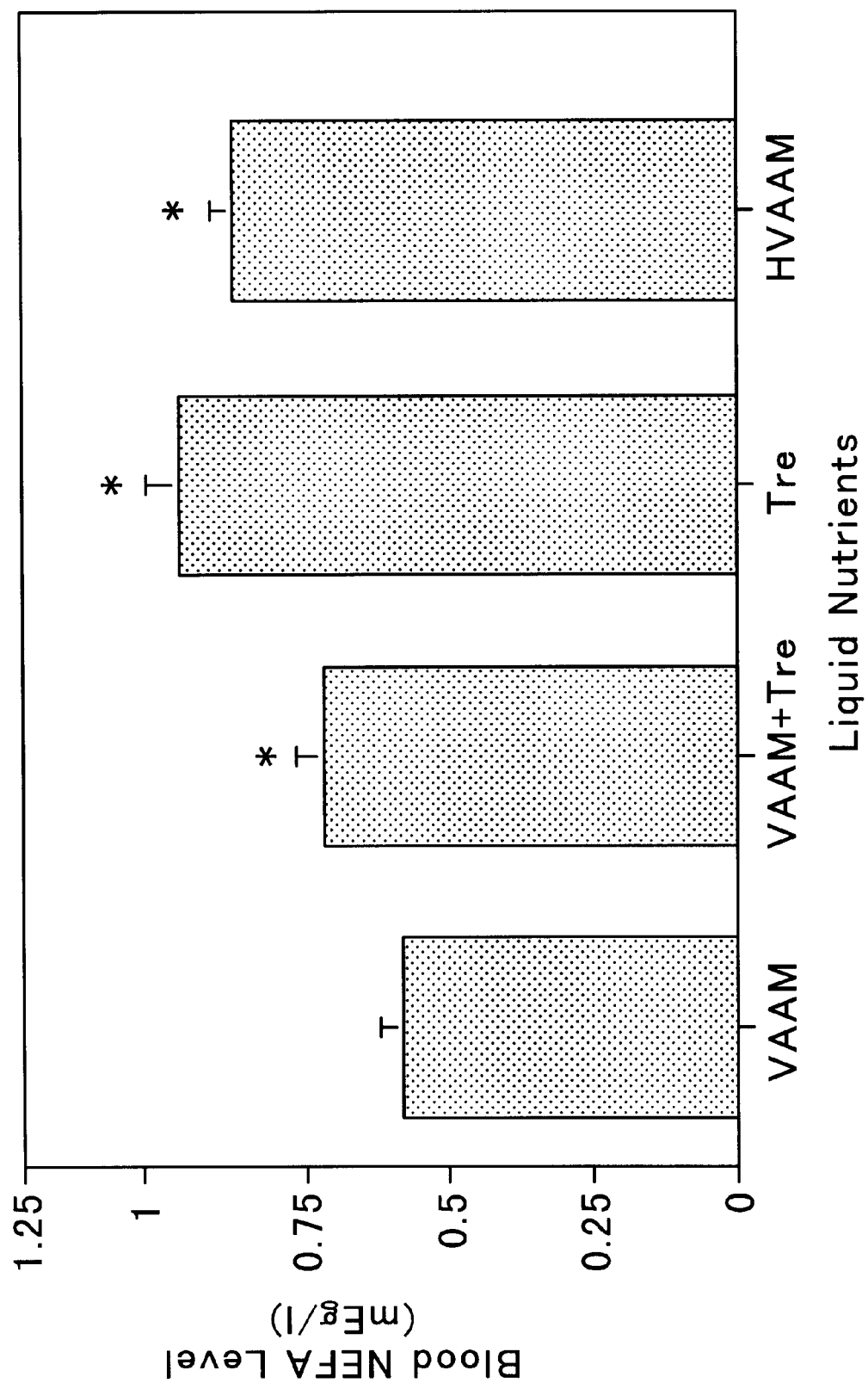

AMINO ACID-TREHALOSE COMPOSITION

BACKGROUND OF THE INVENTION

The present invention relates to an amino acid-sugar composition developed on the basis of the knowledge obtained from a study of a composition which comprises amino acids contained in the saliva secreted by the larvae of a wasp (belonging to the genus Vespa) and more particularly to an amino acid-sugar composition as well as a liquid complement containing the same, which show effects of compensating the reduction of the blood level of amino acids associated with severe exercise, of improving the exercise, of reducing the degree of fatigue after exercise and of recovering from fatigue.

The inventors of this invention have made researches on the saliva secreted by the larvae of various kinds of wasps and have made it clear that the liquid nutrient of the wasp permits the control of the formation of substances which become a cause of the fatigue during exercise, prevention of any reduction of the blood sugar level and the improvement of the moving ability (see Japanese Patent No. 2,518,692). Moreover, it has been elucidated that the working mechanism of the liquid nutrient is to accelerate the use of fats as energy sources for exercise (Abe, et al., J. Physical Fitness & Sports Med., 1995, 44:225). There have also been suggested that Vespa amino acid mixture (VAAM) which is a main component of the liquid nutrient shows a variety of effects such as recovery from fatigue associated with exercise, in addition to the aforementioned functions (see, for instance, Japanese Un-Examined Patent Publication (hereunder referred to as "J.P. KOKAI") Nos. Hei 4-95026, Hei 4-112825, Hei 6-336426 and Hei 6-336432).

On the other hand, it has been well-known that the amino acid balance in the blood is put into disorder due to the fatigue associated with exercise (see T. Bazzarre et al., J. Am. Collage Nutr., 1992, 11:531). It has been believed that the balance is destroyed since the somatic tissues are destroyed and/or worn due to the stress associated with exercise. Up to now, however, the physiological meaning and significance thereof have never attracted special interest.

The inventors have further investigated the amino acid concentration in the blood observed after exercise and the amino acid composition of VAAM and as a result, have found that the amino acid composition of VAAM is correlated to the blood amino acids reduced due to fatigue after exercise. In other words, it has been found that the amino acids severely reduced in a person fatigued from exercise are present in VAAM in a higher concentration. For this reason, it is believed that the supplementation of these amino acids consumed during exercise is indispensable to the improvement of exercise and quick recovery from fatigue (J. P. KOKAI No. Hei 9-249556).

On the other hand, it has been demonstrated that trehalose can induce a considerable increase in the concentration of a non-esterified fatty acid (NEFA) in the mouse serum during exercise (J.P. KOKAI No. Hei 5-186353). In this regard, the liquid nutrient of the wasp includes a considerable amount of trehalose (Abe, et al., Comp. Biochem. Physiol., 1991, 99C:79). Thus, it is expected that the simultaneous administration of trehalose and VAAM permit higher improvement of the exercise.

SUMMARY OF THE INVENTION

Accordingly, it is an object of the present invention to provide an amino acid-sugar composition having effects of compensating the reduction of the blood level of amino acids associated with vigorous exercise, of improving the exercise, of relieving the degree of fatigue after exercise and of recovering from fatigue and in particular a liquid complement containing the same.

It is another object of the present invention to provide a method for controlling any change in the amino acid concentration in the blood, which is observed after vigorous exercise, and for ensuring a desired high level thereof as well as an amino acid-sugar composition, in particular, a liquid complement containing the same.

According to an aspect of the present invention, there is provided an amino acid-sugar composition which comprises an amino acid composition containing proline, alanine, glycine, valine, threonine, leucine, histidine, lysine, isoleucine, arginine, phenylalanine, tyrosine, and tryptophan; and sugar of trehalose.

According to another aspect of the present invention, there is also provided a liquid complement containing the foregoing amino acid-sugar composition.

According to a further aspect of the present invention, there is provided a method for controlling any change in the amino acid concentration of the blood associated with severe exercise, which comprises the step of administering an effective amount of the foregoing amino acid-sugar composition to an animal, in particular a mammal including human.

BRIEF DESCRIPTION OF THE DRAWINGS

FIG. 3 is a bar graph showing the free fatty acid level in blood observed after administering a variety of liquid nutrients to mice and then making the animal swim. The symbol "*" means that the corresponding value has a significant difference ($p<0.05$) with respect to the groups to which VAAM is administered.

DESCRIPTION OF THE PREFERRED EMBODIMENTS

Figure 1:
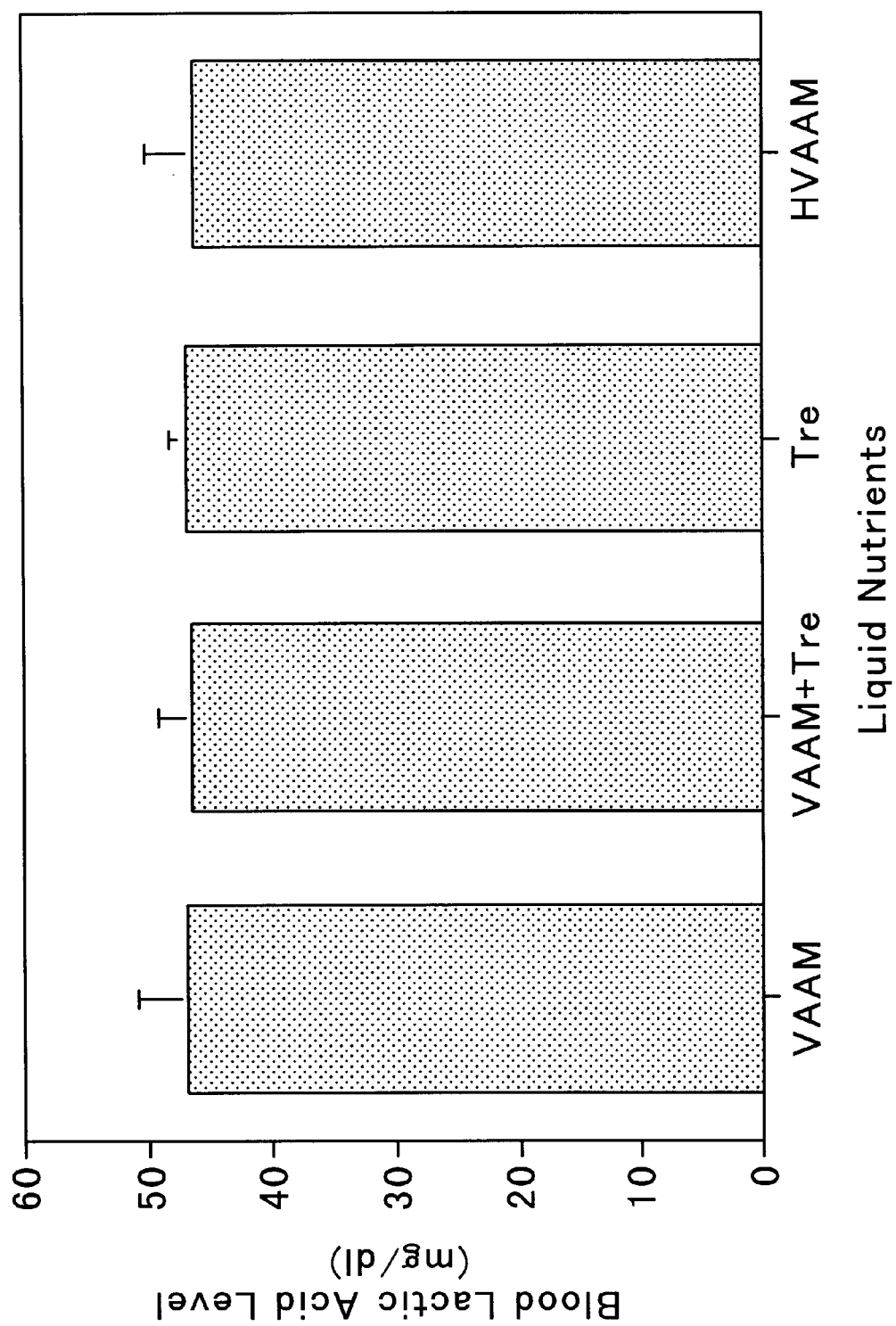
FIG. 1 is a bar graph showing the lactic acid level in the blood observed after administering a variety of liquid nutrients to mice and then making the animal swim.

According to a preferred embodiment of the present invention, the amino acid-sugar composition comprises at least one member selected from the group consisting of aspartic acid, serine, glutamic acid and methionine, in addition to the foregoing essential components. According to a more preferred embodiment of the present invention, the amino acid-sugar composition further comprises at least one member selected from the group consisting of taurine, β-alanine, γ-aminobutyric acid, ethanolamine, ammonia, ornithine, 1-methylhistidine, and 3-methylhistidine.

In the amino acid-sugar composition of the present invention, the weight ratio of the amino acid composition to the trehalose preferably falls within the range: 0.45–1.6/0.5–5.0 and more preferably 0.8–1.6/1.0–4.0.

The amino acid-sugar composition of the present invention comprises an amino acid composition and trehalose, as has been discussed above.

The amino acid composition used in the amino acid-sugar composition of the invention is preferably those comprising 4 to 30 moles of proline, 4 to 16 moles of alanine, 7 to 25 moles of glycine, 4 to 16 moles of valine, 2 to 15 moles of threonine, 2 to 12 moles of leucine, 1 to 12 moles of histidine, 5 to 12 moles of lysine, 3 to 9 moles of isoleucine, 2 to 5 moles of arginine, 0.5 to 5 moles of phenylalanine, 1 to 9 moles of tyrosine, and 1 to 5 moles of tryptophan.

The amino acid composition used in the amino acid-sugar composition of the invention is more preferably those (VAAM) comprising 4 to 30 moles of proline, 4 to 12 moles of alanine, 7 to 20 moles of glycine, 4 to 8 moles of valine, 2 to 15 moles of threonine, 2 to 12 moles of leucine, 1 to 5 moles of histidine, 5 to 11 moles of lysine, 3 to 9 moles of isoleucine, 2 to 5 moles of arginine, 0.5 to 5 moles of phenylalanine, 1 to 9 moles of tyrosine, 1 to 5 moles of tryptophan and 0.1 to 5 moles of methionine.

Preferably used herein further include the foregoing compositions (VAAM) which further comprise not more than 1 mole of aspartic acid, not more than 5 moles of serine and not more than 4 moles of glutamic acid.

Preferably used herein also include the foregoing compositions which further comprise not more than 3 moles of taurine, not more than one mole of β-alanine, not more than 0.5 mole of γ-aminobutyric acid, not more than 3 moles of ethanolamine, not more than 2 moles of ammonia, not more than 3 moles of ornithine, not more than one mole of 1-methylhistidine, and not more than one mole of 3-methylhistidine.

The particularly preferred amino acid composition used in the amino acid-sugar composition of the invention is those (HVAAM) comprising 12.6 to 23.4 moles of proline, 8.4 to 15.6 moles of alanine, 13.3 to 24.9 moles of glycine, 8.2 to 15.4 moles of valine, 5.0 to 9.4 moles of threonine, 4.3 to 8.1 moles of leucine, 1.8 to 11.9 moles of histidine, 1.7 to 3.3 moles of serine, 6.0 to 11.2 moles of lysine, 3.1 to 5.9 moles of isoleucine, 2.2 to 10.4 moles of glutamic acid, 2.4 to 4.6 moles of arginine, 2.6 to 5.0 moles of phenylalanine, 4.2 to 7.8 moles of tyrosine, and 1.5 to 2.9 moles of tryptophan.

More preferred HVAAM has the following composition: 14.4 to 21.6 moles of proline, 9.6 to 14.4 moles of alanine, 15.2 to 23.0 moles of glycine, 9.4 to 14.2 moles of valine, 5.8 to 8.7 moles of threonine, 5.0 to 7.5 moles of leucine, 2.0 to 11.0 moles of histidine, 2.0 to 3.0 moles of serine, 6.8 to 10.4 moles of lysine, 3.6 to 5.4 moles of isoleucine, 2.5 to 9.6 moles of glutamic acid, 2.8 to 4.2 moles of arginine, 3.0 to 4.6 moles of phenylalanine, 4.8 to 7.2 moles of tyrosine, and 1.7 to 2.7 moles of tryptophan.

The composition of the particularly preferred HVAAM is as follows: 16.2 to 19.8 moles of proline, 10.8 to 13.2 moles of alanine, 17.1 to 21.1 moles of glycine, 10.6 to 13.0 moles of valine, 6.4 to 8.0 moles of threonine, 5.5 to 6.8 moles of leucine, 2.3 to 10.1 moles of histidine, 2.2 to 2.8 moles of serine, 7.7 to 9.5 moles of lysine, 4.0 to 5.0 moles of isoleucine, 2.8 to 8.8 moles of glutamic acid, 3.1 to 3.9 moles of arginine, 3.4 to 4.2 moles of phenylalanine, 5.4 to 6.6 moles of tyrosine, and 1.9 to 2.5 moles of tryptophan.

In the amino acid composition (HVAAM) used in the present invention, the molar amount of histidine preferably ranges from 6.4 to 11.9 moles, more preferably 7.2 to 11.0 moles and most preferably 8.1 to 10.1 moles. In addition, the molar amount of glutamic acid preferably ranges from 5.6 to 10.4 moles, more preferably 6.4 to 9.6 moles and most preferably 7.2 to 8.8 moles.

The amino acid composition (HVAAM) used in the present invention may comprise, in addition to the foregoing amino acids, methionine (in an amount preferably ranging from 0.3 to 0.7 mole % and more preferably 0.4 to 0.6 mole %), aspartic acid (in an amount preferably ranging from 0.1 to 0.3 mole %), taurine (Tau) (in an amount of preferably not more than 3 mole %), phospho-ethanolamine (P-EtAm) (in an amount of preferably not more than 2 mole %), cystine (Cys) (in an amount of preferably not more than 0.5 mole %), β-alanine (β-Ala) (in an amount of preferably not more than one mole %), γ-aminobutyric acid (GABA) (in an amount of preferably not more than 0.5 mole %), ornithine (Orn) or ethanolamine (EtAm) (in an amount of preferably not more than 3 mole %), ammonia ($NH_3$) (in an amount of preferably not more than 2 mole %), 1-methylhistidine (1-MeHis) (in an amount of preferably not more than 3 mole %), 3-methylhistidine (3-MeHis) (in an amount of preferably not more than 1 mole %).

The amino acids present in the amino acid composition used in the invention are particularly preferably L-amino acids.

The amino acid composition of the present invention may be prepared by mixing the foregoing amino acids commercially available in a desired mixing ratio specified above. Moreover, if the composition is used in the form of a liquid complement, it is sufficient to dissolve the composition in water. In general, the composition is prepared in the form of a uniform powdery mixture and may be dissolved in water prior to the practical use thereof. The temperature for preparing and storing the composition of the present invention is not restricted to any specific range, but the composition is preferably prepared and stored at a temperature of not more than room temperature. The composition of the invention has a slightly bitter taste, does not have any toxicity even when administering it to a mouse at a level of 20 g/kg and the $LD_{50}$ value thereof is much higher than 20 g/kg.

The composition of the present invention may effectively be used in medicines and foods such as beverages. If it is used in the form of a medicine, the dosage form thereof is not restricted to any specific one. Thus, the composition may be used in any dosage form and administered through the usual routes. For instance, it may be administered orally, through rectum, through injection and transfusion. If it is orally administered, the composition may be used in the form of a composition containing the ingredients defined above or in the form of pharmaceutical preparations, which comprises the composition in combination with pharmaceutically acceptable carriers and/or vehicles, such as tablets, capsules, powders, troches and syrups. However, the composition is preferably in the dosage form of, for instance, a liquid preparation and administered orally, since the absorption of the composition by the body may require a long period of time if it is used in the form of a solid preparation such as a tablet or a powder. In this case, the composition is preferably administered in the form of an aqueous solution along with an appropriate additive, for instance, a salt such as sodium chloride, a buffering agent and/or a chelating agent. If the composition is used as an injection, an appropriate buffering agent, an isotonizing agent or the like may be added to the composition, then the resulting mixture is dissolved in sterilized distilled water to give an injectable solution and the solution may be intravenously administered through, for instance, instillation.

If it is used as a food, the composition to which a flavor is given may be formed into a drink such as a refreshing beverage or a powdered drink such as those prepared by drying the mixture through a spray-drying, freeze-drying or micro fine powder-forming method to give powder and then encapsulating it in a capsule, or a tablet.

The composition of the present invention has quite low toxicity and therefore, the dose thereof may widely vary. The dose may depend upon the mode (route) of administration and the intended purposes of the composition, but the amount of the solid content thereof ranges from 1 to 12 g/unit dose or 3 to 18 g/day, preferably 2 to 4 g/unit dose or 6 to 12 g/day.

If the composition is used in the form of a liquid complement before, during and/or after exercise, the composition is used or administered in the form of a solution having a concentration of 0.8 to 3.8% by weight in an amount ranging from 200 to 500 ml/unit dose over 1 to 3 times per day. The injectable solution may be a 0.8 to 3.8% by weight aqueous solution and may be administered in a unitary dose ranging from 100 to 400 ml and preferably 150 to 300 ml.

The present invention will hereinafter be described in more detail with reference to the following working Examples and Test Examples, but the present invention is not restricted to these specific Examples at all.

EXAMPLE 1

There were dissolved, in distilled water, amino acid components (total amount: 1.8 g) in the form of an amino acid composition (VAAM) listed in the following Table 1 and 2.0 g of trehalose to give an aqueous solution (3.8 g/100 ml).

Test Example

This test was performed in order to demonstrate the effect of the amino acid-sugar composition of the present invention, i.e., the reduction of exercise load during sustaining exercise and more specifically, the test was an experiment carried out using mice to which the composition was administered prior to the initiation of the exercise.

This experiment was carried out according to the method disclosed in Jpn. J. Phys. Fitness Sports Med., 1995, 44:225–238. More specifically, mice (male; ddY) (6-week-old; 5 animals per group) were fasted at room temperature for 16 hours, followed by oral administration of a 1.8% by weight aqueous solution containing the composition VAAM or HVAAM as set forth in Table 1 or trehalose; or an aqueous solution containing 1.8% by weight of VAAM and 2% by weight of trehalose in an amount of 37.5 µl/g body weight and thereafter giving the mice a rest at room temperature for 30 minutes. Then the mice were made to swim in a running water pool (a water tank having a diameter of 32 cm and a depth of 30 cm, which was filled with water maintained at 35° C. and in which the water was circulated at a rate of 8 m/min using a circulator) for 30 minutes. After making the mouse swim, they were inspected for the lactic acid level in the blood, the blood sugar (glucose) level and the free fatty acid level in the blood.

The lactic acid level in the blood was determined using a clinical reagent available from Sigma Company, by measuring absorbance at 340 nm due to NADH, each molecule of which was formed when lactic acid was converted into pyruvic acid because of the action of lactic acid dehydrogenase. The free fatty acid level in the serum was determined by centrifuging the collected blood and then quantitatively analyzing the fatty acids present in the supernatant. More specifically, the hydrogen peroxide formed by the action of acyl-CoA synthetic enzyme and acyl-CoA oxidase was reacted with a peroxidase. followed by determination of the absorbance at 550 nm due to the stained 3-methyl-N-ethyl-N-(2-hydroxyethyl)aniline and 4-aminoantipyrine to thus determine the free fatty acid level.

The results thus obtained are summarized in the following Table 2 and the attached FIGS. 1, 2 and 3.

TABLE 1

| Kind of Amino Acid | Concentration (Molar Ratio) of Amino Acid | |
| --- | --- | --- |
| | VAAM | HVAAM |
| Pro | 18.00 | 18.00 |
| Ala | 6.00 | 12.00 |
| Gly | 19.10 | 19.10 |
| Val | 5.90 | 11.80 |
| Thr | 7.20 | 7.20 |
| Leu | 6.20 | 6.20 |
| His | 2.60 | 2.60 |
| Ser | 2.50 | 2.50 |
| Lys | 8.60 | 8.60 |
| Ile | 4.50 | 4.50 |
| Glu | 3.20 | 3.20 |
| Arg | 3.50 | 3.50 |
| Met | 0.50 | 0.50 |
| Asp | 0.20 | 0.20 |
| Phe | 3.80 | 3.80 |
| Tyr | 6.00 | 6.00 |
| Trp | 2.20 | 2.20 |

TABLE 2

| | VAAM | VAAM + Tre | Tre | HVAAM |
| --- | --- | --- | --- | --- |
| Lactic Acid Level (mg/dl) | 46.72 ± 4.06 | 46.27 ± 2.72 | 46.69 ± 1.19 | 45.74 ± 3.87 |
| Blood Sugar Level (mg/dl) | 74.34 ± 3.67 | 86.59 ± 2.49 | 83.14 ± 3.45 | 94.89 ± 3.65 |
| NEFA (mEq/l) | 0.58 ± 0.01 | 0.72 ± 0.05 | 0.97 ± 0.06 | 0.87 ± 0.04 |

The groups of mice to which HVAAM, trehalose (Tre) and VAAM+trehalose were administered, respectively did not show any significant difference in the lactic acid level in the blood observed after applying thereto the load of swimming over 30 minutes, as compared with that observed for the group to which VAAM was administered (see FIG. 1).

Figure 2:
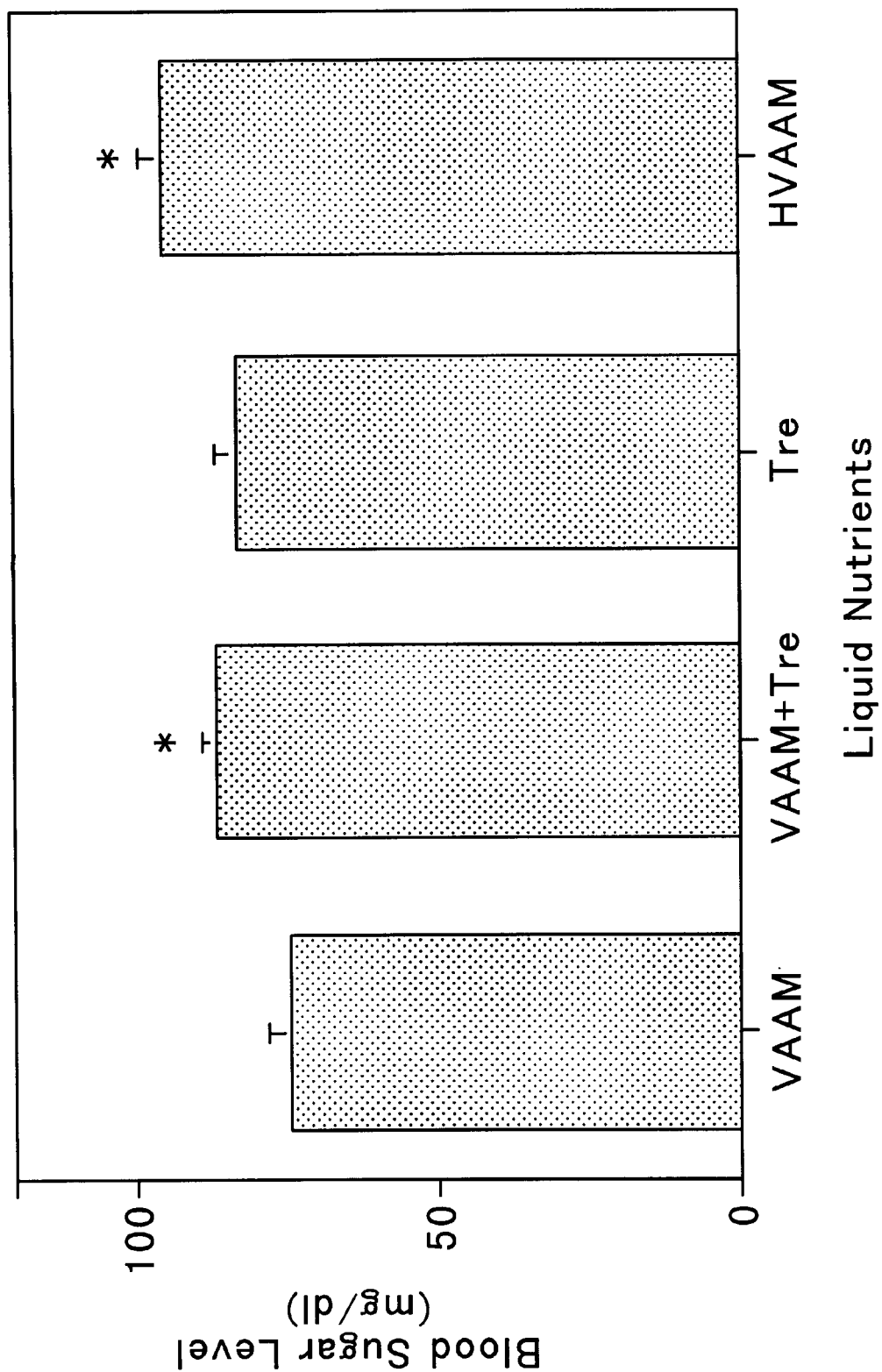
FIG. 2 is a bar graph showing the blood sugar level observed after administering a variety of liquid nutrients to mice and then making the animal swim. The symbol "*" means that the corresponding value has a significant difference ($p<0.05$) with respect to the groups to which VAAM is administered.

On the other hand, the groups of mice to which 1.8% VAAM+2% trehalose and 1.8% HVAAM were administered, respectively showed the blood sugar levels significantly higher than that observed for the group to which 1.8% VAAM was administered (see FIG. 2). Moreover, the groups to which 1.8% VAAM+2% trehalose; 2% trehalose; and 1.8% HVAAM were administered, respectively also showed the free fatty acid levels in the blood significantly higher than that observed for the group to which 1.8% VAAM was administered (see FIG. 3).

The foregoing results clearly indicate that the mixture of trehalose with VAAM and HVAAM not only suppress the increase of the lactic acid level in the blood during exercise to an extent almost comparable to that observed for VAAM, but also significantly suppress the reduction of the blood sugar level during exercise as compared with those observed for VAAM or trehalose, and have an effect of significantly increasing the free fatty acid level in the blood. Accordingly, it is clear that the mixture of trehalose with VAAM and HVAAM have an effect of improving the functions superior to the moving ability-improving effect of VAAM.

As has been described above in detail, the composition of the present invention has effects of compensating the reduction of the blood level of amino acids associated with severe exercise, of improving the exercise, of reducing the degree of fatigue after exercise and of recovering from fatigue. In addition, the administration of the composition of the present invention permits the inhibition of the consumption of amino acids associated with exercise and any induction of fatigue accompanied by exercise.

What is claimed is:

1. A method for compensating for the reduction of amino acid blood levels associated with vigorous exercise, comprising administering to an animal in need thereof an effective amount of an amino acid-trehalose composition which comprises an amino acid composition comprising proline, alanine, glycine, valine, threonine, leucine, histidine, lysine, isoleucine, arginine, phenylalanine, tyrosine, and tryptophan; and trehalose, wherein the amino acid composition comprises 4 to 30 moles of proline, 4 to 16 moles of alanine, 7 to 25 moles of glycine, 4 to 16 moles of valine, 2 to 15 moles of threonine, 2 to 12 moles of leucine, 1 to 12 moles of histidine, 5 to 12 moles of lysine, 3 to 9 moles of isoleucine, 2 to 5 moles of arginine, 0.5 to 5 moles of phenylalanine, 1 to 9 moles of tyrosine, and 1 to 5 moles of trytophan to compensate for the reduction of amino acid blood levels.

2. The method of claim 1 wherein the animal is a mammal.

3. The method of claim 2 wherein the mammal is human.

4. The method of claim 1, wherein said amino acid-trehalose composition further comprises at least one member selected from the group consisting of aspartic acid, serine, glutamic acid and methionine.

5. The method of claim 1, wherein said amino acid-trehalose composition further comprises at least one member selected from the group consisting of taurine, β-alanine, γ-aminobutyric acid, ethanolamine, ammonia, ornithine, 1-methylhistidine, and 3-methylhistidine.

6. The method of claim 1, wherein the weight ratio of the amino acid composition to trehalose falls within the range: 0.45–1.6/0.5–5.0.

7. The method of claim 1, wherein the amino add composition comprises 4 to 30 moles of proline, 4 to 12 moles of alanine, 7 to 20 moles of glycine, 4 to 8 moles of valine, 2 to 15 moles of threonine, 2 to 12 moles of leucine, 1 to 5 moles of histidine, 5 to 11 moles of lysine, 3 to 9 moles of isoleucine, 2 to 5 moles of arginine, 0.5 to 5 moles of phenylalanine, 1 to 9 moles of tyrosine, 1 to 5 moles of tryptophan and 0.1 to 5 moles of methionine.

8. The method of claim 1, wherein the amino acid composition further comprises not more than 1 mole of aspartic acid, not more than 5 moles of serine and not more than 4 moles of glutamic acid.

9. The method of claim 1, wherein the amino acid composition further comprises not more than 3 moles of taurine, not more than 1 mole of β-alanine, not more than 0.5 mole of γ-butyric acid, not more than 3 moles of ethanolamine, not more than 2 moles of ammonia, not more than 3 moles of ornithine, not more than 1 mole of 1-methylhistidine, and not more than 1 mole of 3-methylhistidine.

10. The method of claim 1, wherein said amino acid-trehalose composition is in the form of a transfusion.

11. A method for suppressing the reduction of the blood sugar level during exercise a comprising administering to an animal in need thereof an effective amount of an amino acid-trehalose composition which comprises an amino acid composition comprising proline, alanine, glycine, valine, threonine, leucine, histidine, lysine, isoleucine, arginine, phenylalanine, tyrosine, and tryptophan; and trehalose, wherein the amino acid composition comprises 4 to 30 moles of proline, 4 to 16 moles of alanine, 7 to 25 moles of glycine, 4 to 16 moles of valine, 2 to 15 moles of threonine, 2 to 12 moles of leucine, 1 to 12 moles of histidine, 5 to 12 moles of lysine, 3 to 9 moles of isoleucine, 2 to 5 moles of arginine, 0.5 to 5 moles of phenylalanine, 1 to 9 moles of tyrosine, and 1 to 5 moles of trytophan to compensate for the reduction of amino acid blood levels.

12. The method of claim 11, wherein the animal is a mammal.

13. The method of claim 11, wherein the mammal is human.

14. The method of claim 11, wherein said amino acid-trehalose composition further comprises at least one member selected from the group consisting of aspartic acid, serine, glutamic acid and methionine.

15. The method of claim 11, wherein said amino acid-trehalose composition further comprises at least one member selected from the group consisting of taurine, β-alanine, γ-aminobutyric acid, ethanolamine, ammonia, ornithine, 1-methylhistidine, and 3-methylhistidine.

16. The method of claim 11; wherein the weight ratio of the amino acid composition to trehalose falls within the range: 0.45–1.6/0.5–5.0.

17. The method of claim 11, wherein the amino add composition comprises 4 to 30 moles of proline, 4 to 12 moles of alanine, 7 to 20 moles of glycine, 4 to 8 moles of valine, 2 to 15 moles of threonine, 2 to 12 moles of leucine, 1 to 5 moles of histidine, 5 to 11 moles of lysine, 3 to 9 moles of isoleucine, 2 to 5 moles of arginine, 0.5 to 5 moles of phenylalanine, 1 to 9 moles of tyrosine, 1 to 5 moles of tryptophan and 0.1 to 5 moles of methionine.

18. The method of claim 11, wherein the amino acid composition further comprises not more than 1 mole of aspartic acid, not more than 5 moles of serine and not more than 4 moles of glutamic acid.

19. The method of claim 11, wherein the amino acid composition further comprises not more than 3 moles of taurine, not more than 1 mole of β-alanine, not more than 0.5 mole of γ-butyric acid, not more than 3 moles of ethanolamine, not more than 2 moles of ammonia, not more than 3 moles of ornithine, not more than 1 mole of 1-methyihistidine, and not more than 1 mole of 3-methylhistidine.

20. A method for increasing free fatty acid levels in the blood during exercise comprising administering to an animal in need thereof an effective amount of an amino acid-trehalose composition comprising an amino acid composition which comprises proline, alanine, glycine, valine, threonine, leucine, histidine, lysine, isoleucine, arginine, phenylalanine, tyrosine, and tryptophan; and trehalose, wherein the amino acid composition comprises 4 to 30 moles of proline, 4 to 16 moles of alanine, 7 to 25 moles of glycine, 4 to 16 moles of valine, 2 to 15 moles of threonine, 2 to 12 moles of leucine, 1 to 12 moles of histidine, 5 to 12 moles of lysine, 3 to 9 moles of isoleucine, 2 to 5 moles of arginine, 0.5 to 5 moles of phenylalanine, 1 to 9 moles of tyrosine, and 1 to 5 moles of trytophan to compensate for the reduction of amino acid blood levels.

21. The method of claim 20, wherein the animal is a mammal.

22. The method of claim 20, wherein the mammal is human.

23. The method of claim 20, wherein said amino acid-trehalose composition further comprises at least one member selected from the group consisting of aspartic acid, serine, glutamic acid and methionine.

24. The method of claim 20, wherein said amino acid-trehalose composition further comprises at least one member selected from the group consisting of taurine, β-alanine, γ-aminobutyric acid, ethanolamine, ammonia, ornithine, 1-methylhistidine, and 3-methylhistidine.

25. The method of claim 20, wherein the weight ratio of the amino acid composition to trehalose falls within the range: 0.45–1.6/0.5–5.0.

26. The method of claim 20, wherein the amino add composition comprises 4 to 30 moles of proline, 4 to 12 moles of alanine, 7 to 20 moles of glycine, 4 to 8 moles of valine, 2 to 15 moles of threonine, 2 to 12 moles of leucine, 1 to 5 moles of histidine, 5 to 11 moles of lysine, 3 to 9 moles of isoleucine, 2 to 5 moles of arginine, 0.5 to 5 moles of phenylalanine, 1 to 9 moles of tyrosine, 1 to 5 moles of tryptophan and 0.1 to 5 moles of methionine.

27. The method of claim 20, wherein the amino acid composition further comprises not more than 1 mole of aspartic acid, not more than 5 moles of serine and not more than 4 moles of glutamic acid.

28. The method of claim 20, wherein the amino acid composition further comprises not more than 3 moles of taurine, not more than 1 mole of β-alanine, not more than 0.5 mole of γ-butyric acid, not more than 3 moles of ethanolamine, not more than 2 moles of ammonia, not more than 3 moles of ornithine, not more than 1 mole of 1-methylhistidine, and not more than 1 mole of 3-methylhistidine.

* * * * *